United States Patent
Mitchell

(10) Patent No.: US 10,219,996 B2
(45) Date of Patent: Mar. 5, 2019

(54) COMPOSITION FOR SKIN

(71) Applicant: Deborah Mitchell, Shifnal (GB)

(72) Inventor: Deborah Mitchell, Shifnal (GB)

(*) Notice: Subject to any disclaimer, the term of this patent is extended or adjusted under 35 U.S.C. 154(b) by 0 days.

(21) Appl. No.: 14/913,832

(22) PCT Filed: Aug. 23, 2013

(86) PCT No.: PCT/GB2013/052237
§ 371 (c)(1),
(2) Date: Feb. 23, 2016

(87) PCT Pub. No.: WO2015/025112
PCT Pub. Date: Feb. 26, 2015

(65) Prior Publication Data
US 2016/0206552 A1  Jul. 21, 2016

(51) Int. Cl.
| *A61K 35/64* | (2015.01) |
| *A61K 8/98* | (2006.01) |
| *A61Q 19/00* | (2006.01) |
| *A61Q 19/08* | (2006.01) |
| *A61K 8/02* | (2006.01) |
| *A61K 8/04* | (2006.01) |
| *A61K 8/49* | (2006.01) |
| *A61K 8/97* | (2017.01) |
| *A61K 9/00* | (2006.01) |
| *A61K 9/107* | (2006.01) |
| *A61K 35/644* | (2015.01) |
| *A61K 47/22* | (2006.01) |
| *A61Q 19/06* | (2006.01) |
| *A61K 35/63* | (2015.01) |

(52) U.S. Cl.
CPC .......... *A61K 8/987* (2013.01); *A61K 8/0212* (2013.01); *A61K 8/04* (2013.01); *A61K 8/49* (2013.01); *A61K 8/97* (2013.01); *A61K 8/988* (2013.01); *A61K 9/0014* (2013.01); *A61K 9/107* (2013.01); *A61K 35/63* (2015.01); *A61K 35/64* (2013.01); *A61K 35/644* (2013.01); *A61K 47/22* (2013.01); *A61Q 19/00* (2013.01); *A61Q 19/06* (2013.01); *A61Q 19/08* (2013.01); *A61K 2800/30* (2013.01)

(58) Field of Classification Search
None
See application file for complete search history.

(56) References Cited

U.S. PATENT DOCUMENTS

| 2011/0294731 A1* | 12/2011 | Torfi | A61Q 19/08 514/7.6 |
| 2012/0082656 A1* | 4/2012 | Yoon | A61K 9/0019 424/94.6 |
| 2012/0128784 A1* | 5/2012 | Han | A61K 8/987 424/537 |

FOREIGN PATENT DOCUMENTS

| CN | 1268348 A | * | 10/2000 |
| CN | 102973483 A | | 3/2013 |
| CN | 102988263 A | * | 3/2013 |
| FR | 2900026 A1 | | 10/2007 |
| GB | 2469154 A | | 10/2010 |
| RU | 2005105960 A | * | 8/2006 |

OTHER PUBLICATIONS

Marz (Insect Biochemistry (1981), vol. 11, No. 6, pp. 685-690).*
International Search Report and Written Opinion; International Application No. PCT/GB2013/052237; International Filing Date: Aug. 23, 2013; dated Jun. 23, 2014; 12 pages.
Database GNPD [Online], "Mintel" Jun. 30, 2013 "Facemask" XP002724280, Database accession No. 2070265 Product Description & Ingredients, 6 pgs.
Marz, R. et al., "Queen bee venom contains much less phospholipase than worker bee venom," Insect Biochemistry, vol. 11, No. 6, Jan. 1, 1981 pp. 685-690.
Bee Venom Moisture and Anti-Wrinkle Face Mask, Jun. 11, 2013, https://www.nzivgou.com/bee-venom-mask?product_id=4&product_details_id=59.
Royal Nectar Bee Venom Mask Royal Bee Venom Mask, Jun. 20, 2012, http://www.newzealandmade.com/store/nzsouvenirs/index.php/product-details/450.
Translation of the Official Action for Taiwanese Patent Application No. 103127206 dated Jun. 27 2018, 12 pages.

* cited by examiner

*Primary Examiner* — Susan Hoffman
(74) *Attorney, Agent, or Firm* — Cantor Colburn LLP

(57) ABSTRACT

The invention provides a composition suitable for topical skin application comprising isolated queen bee venom. The queen bee venom has been found to be significantly superior for treating skin conditions relative to the normal bee venom. Therefore the invention also provides a method of treatment or prevention of a skin condition, comprising the topical application of the composition onto the skin of a subject afflicted with the skin condition, or at risk of being afflicted with the skin condition. The skin condition could be skin ageing, elastosis, laxity (sagging), rhytids (wrinkles), skin infection, skin damage, skin burn, pain, and muscle tightness, or combinations thereof.

23 Claims, 1 Drawing Sheet

Before:
After:

COMPOSITION FOR SKIN

FIELD OF THE INVENTION

The present invention relates to the field of skin cosmetics and treatment, in particular compositions for topical skin application and uses thereof.

BACKGROUND TO THE INVENTION

Topical creams, ointments and pastes have been used for centuries to help alleviate skin conditions such as burns, infection and damage. Many products are also available to revitalize aging skin or reduce wrinkles.

Ageing skin can be particularly prone to damage and loss of elasticity. With aging, the outer skin layer (epidermis) thins, becomes more pale and translucent. Changes in the connective tissue reduce the skin's strength and elasticity. This is especially pronounced in sun-exposed areas (solar elastosis). Elastosis produces the leathery, weather-beaten appearance common to people who spend a large amount of time outdoors. With ageing, the blood vessels of the dermis become more fragile, leading to bruising, bleeding under the skin, cherry angiomas, and similar conditions. Sebaceous glands produce less oil with age, making it harder to keep the skin moist, resulting in dryness and itchiness. Aging skin also repairs itself more slowly than younger skin. Wound healing in aged skin is slower, which contributes to pressure ulcers and infections.

One recognised anti-ageing ingredient is honey bee venom, otherwise known as apitoxin. The honey bee venom is used in anti-wrinkle creams and masks, where it is considered to be a non-invasive face-lift and a more natural alternative to cosmetic procedures that involve injection of agents such as the Botulinum toxin. The active portion of the venom is a complex mixture of proteins, which causes local inflammation and acts as an anticoagulant. The venom is produced in the abdomen of worker bees from a mixture of acidic and basic secretions. The main component is melittin, which usually comprises about 52% of the venom peptides. Melittin is a strong anti-inflammatory agent and induces the production of cortisol in the body.

An aim of the invention is to provide an improved composition to alleviate the appearance of skin conditions such as skin ageing and skin damage. The composition may in particular be used for cosmetic application, to improve the appearance of the skin.

SUMMARY OF THE INVENTION

According to a first aspect of the present invention, there is provided a composition suitable for topical skin application comprising isolated queen bee venom.

Advantageously, the queen bee venom has been found to be significantly superior for treating skin conditions relative to the normal bee venom.

Unlike normal bee venom, the queen bee venom is not aggressive venom. It is used to protect eggs and larvae in the hive. The combs where eggs are laid are sealed with queen bee venom to keep the area disease free. It has a high content of natural antibiotic and cortisol, an anti-inflammatory. Queen bee venom has a stronger paralysis effect than normal bee venom due to higher concentrations of melittin.

As the name suggests, the queen bee venom is produced in the abdomen of queen bees from a mixture of acidic and basic secretions.

Surprisingly, the queen bee venom products have been found to have excellent properties in terms of anti-aging and anti-inflammation. It provides unexpectedly greater beneficial properties for topical skin application relative to normal bee venom.

According to another aspect of the present invention, there is provided a pharmaceutical composition for topical application to the skin, comprising the composition of the invention herein, and a pharmaceutically acceptable excipient or carrier.

According to another aspect of the present invention, there is provided a method of treatment or prevention of a skin condition, comprising the topical application of the composition according to the invention herein onto the skin of a subject afflicted with the skin condition, or at risk of being afflicted with the skin condition.

According to another aspect of the present invention, there is provided a composition according to the invention herein for use as a medicament.

According to another aspect of the present invention, there is provided a composition according to the invention herein for use in the treatment or prevention of a skin condition selected from: skin ageing, elastosis, laxity (sagging), rhytids (wrinkles), skin infection, skin damage, skin burn, pain, muscle tightness and combinations thereof.

According to another aspect of the present invention, there is provided a use of the composition according to the invention herein as a topical application on skin. The use may be cosmetic use.

According to another aspect of the present invention, there is provided a cosmetic treatment of the skin, comprising the application of the composition according to the invention herein on the skin.

According to another aspect of the present invention, there is provided a face mask incorporating the composition according to the invention herein.

DETAILED DESCRIPTION OF THE INVENTION

The composition of the invention makes use of queen bee venom.

Queen bee venom includes melittin. Melittin is a peptide consisting of 26 amino acids. In a queen bee venom product it will normally be present in a level of above 50%, such as 52% or more, or 55% or more, or 58% or more, or 60% or more, e.g. it may be from 55% up to 80%. This compares to normal bee venom that usually has levels of 40 to 50% melittin. Melittin has antibacterial and anti-inflammatory properties.

Queen bee venom also includes apamin (which is a small basic peptide consisting of 18 amino acids), adolapin, Mast Cell Degranulating Peptide (MCDP or peptide 401), hyluronidase, secapin, tertiapin, and procamine.

In general, whilst the exact composition of queen bee venom varies from region to region and from hive to hive, there is more melittin and more natural antibiotics present than in normal bee venom.

In one embodiment, the queen bee venom used in the invention is organic, i.e. it is obtained from organic bee hives.

The composition of the invention may be provided in any suitable form, for example it may be provided as a liquid, cream, gel, oil or paste, or similar cosmetic base.

In general, the compositions of the present invention are topical compositions that can be provided in a variety of forms, including but not limited to lotions, milks, mousses, serums, sprays, aerosols, foams, sticks, gels, creams and ointments. In one embodiment, the composition is in the form of a spray or gel and in another embodiment the composition is in the form of a lotion, milk or cream.

The composition may be a water-based composition, oil-based composition, or emulsion composition.

Examples of the water-based composition include skin lotions, beauty essences, water-based gels, and the like, while examples of the oil-based composition include cleansing oil and oil-based gels, and the like. Examples of the emulsion composition include creams, skin milks and sunscreen lotions, and the like, where the types of emulsion include oil in water emulsion (o/w), water in oil emulsion (w/o) and multilayer emulsion (e.g. w/o/w, o/w/o).

The skilled person will understand that a queen bee is an adult, mated female that is the dominant reproductive female in a hive or colony of honeybees. The queen bee may be the mother of most, if not all, the bees in the hive.

The composition may be 100% queen bee venom. Alternatively, the composition may comprise other agents, such as a diluent or a carrier, and therefore the composition will comprise less than 100% queen bee venom.

All % amounts stated in the application are by weight, unless stated otherwise.

The composition may comprise at least 0.1% queen bee venom. The composition may comprise at least 0.2% queen bee venom, preferably 0.5% or more queen bee venom, such as 0.6% or more, 0.7% or more, 0.8% or more, or 0.9% or more.

The composition may comprise at least 1% queen bee venom. The composition may comprise at least 5% queen bee venom, or at least 10% queen bee venom, such as 15% or more, 20% or more, 25% or more, 30% or more, 35% or more, 40% or more, or 45% or more. The composition may comprise at least 50% queen bee venom, such as 55% or more, 60% or more, 65% or more, 70% or more, or 75% or more. The composition may comprise at least 80% queen bee venom, such as 85% or more. The composition may comprise at least 90% queen bee venom.

It has been found that even when used at low levels the queen bee venom will still stimulate a positive reaction on the subject's skin.

The composition may comprise up to 90%, or 92%, or 95%, or 97%, or 98% queen bee venom. In one embodiment the composition comprises up to 99% queen bee venom, or up to 99.5% queen bee venom.

In one embodiment the composition may comprise between about 0.1% and about 99% queen bee venom. The composition may comprise between about 0.5% and about 99% queen bee venom. The composition may comprise between about 1% and about 99% queen bee venom. The composition may comprise between about 10% and about 99% queen bee venom. The composition may comprise between about 30% and about 99% queen bee venom. The composition may comprise between about 50% and about 99% queen bee venom.

In one embodiment the composition may comprise between about 0.5% and about 95% queen bee venom. The composition may comprise between about 0.5% and about 90% queen bee venom. The composition may comprise between about 0.5% and about 80% queen bee venom. The composition may comprise between about 0.5% and about 50% queen bee venom.

In one embodiment the composition may comprise between about 1% and about 95% queen bee venom. The composition may comprise between about 1% and about 90% queen bee venom. The composition may comprise between about 1% and about 80% queen bee venom. The composition may comprise between about 1% and about 50% queen bee venom.

In one embodiment the composition may comprise between about 5% and about 95% queen bee venom.

In one embodiment the composition may comprise between about 10% and about 95% queen bee venom.

In one embodiment the composition may comprise between about 15% and about 90% queen bee venom.

In one embodiment the composition may comprise between about 20% and about 90% queen bee venom.

In one embodiment, the composition includes one or more diluent or carrier. These may be selected from cosmetically acceptable diluents and carriers.

The diluent or carrier may be oil or wax based and/or water based.

For example, it may be water based and may comprise de-ionized water, purified water, natural spring water, rose water or the like. In one embodiment de-ionized or purified water is used.

The water based diluent/carrier may be 100% water or it may comprise components other than water, including but not limited to water-soluble moisturizing agents, conditioning agents, anti-microbials, humectants (e.g. glycerin) and/or other water-soluble skin care actives.

In another embodiment, the diluent or carrier may be oil or wax based. The oil may be natural oil or synthetic oil, but preferably is natural oil such as a vegetable oil or a nut oil. The wax is preferably a natural wax.

Combinations of one or more oils and/or one or more waxes may be used.

Liquid oils that can be mentioned include avocado oil, Camellia oil, turtle bean oil, macadamia nut oil, corn oil, mink oil, olive oil, Canoga oil, egg yolk oil, sesame seed oil, Persic oil, wheatgerm oil, Camellia sasanqua oil, castor oil, linseed oil, safflower oil, sunflower oil, grapeseed oil, apricot oil, shea oil, sweet almond oil, cotton oil, evening primrose oil, palm oil, perilla oil, hazelnut oil, soybean oil, peanut oil, tea seed oil, kaya oil, rice bran oil, rapeseed oil, alfalfa oil, Chinese tung tree wood oil, Japanese tung tree wood oil, jojoba oil, germ oil, poppyseed oil, pumpkin oil, blackcurrant oil, millet oil, barley oil, quinoa oil, rye oil, candlenut oil, passionflower oil, musk rose oil, triglycerine, glyceryl trioctanoate, and glyceryl triisopalmitate.

Solid oils/fats that can be mentioned include cocoa butter, coconut butter, horse fat, hardened coconut oil, palm oil, beef tallow, mutton tallow, hardened beef tallow, palm kernel oil, lard, Japan wax kernel oil, hardened oil, Japan wax, shea butter, and hardened castor oil;

Waxes that can be mentioned include beeswax, candelilla wax, carnauba wax, lanolin, lanolin acetate, liquid lanolin, sugar cane wax, fatty acid isopropyl lanolin, hexyl laurate, reduced lanolin, jojoba wax, hard lanolin, polyoxyethylene (hereinafter referred to as POE), lanolin alcohol ether, POE lanolin alcohol acetate, lanolin fatty acid polyethylene glycol, and POE hydrogenated lanolin alcohol ether. In one embodiment the carrier is not lanolin based.

Ester oils that can be mentioned include isopropyl myristate, cetyl octoate, octyldodecil myristate, isopropyl palmitate, butyl stearate, hexyl laurate, myristyl myristate, decyloleate, hexyldecyl dimethyl octoate, cetyl lactate, myristyl lactate, lanolin acetate, isocetyl stearate, isocetyl iso-stearate, 12-hydroxy cholesteryl stearate, di-2-ethylhexylic acid ethyleneglycol, dipentaerythritol fatty acid ester, N-alkylglycol monoisostearate, neopentylglycol dicaprate, diisostearyl malate, glyceryl di-2-heptyl undecanate, tri-methylol propane tri-2-ethylhexyl acid, tri-methylol propane triisostearate, pentaerythritol tetra-2-ethylhexyl acid, glyceryl tri-2-ethyl-hexanoate, tri-methylol propane triisostearate, cetyl-2-ethylexanoate, 2-ethylhexyl-palmitate, glycerine trimyristate, glyceride tri-2-heptyl undecatoic acid, methyl ester of castor oil fatty acid, oleate oil, acetoglyceride, palmitate-2-heptyl undecyl, diisopropyl adipate, N-lauroyl-L-glutamic acid-2-octyldodecil ester, di-2-heptylundecyl adipate, di-2-ethylhexyl sebacate, myristate-2-hexyldecyl, palmitate-2-hexyldecyl, adipate-2-hexyldecyl, diisopropyl sebacate, and succinate-2-ethylhexyl.

Higher fatty acids that can be mentioned include lauric acid, myristic acid, palmitic acid, stearic acid, behenic acid, oleic acid, 12-hydroxy-stearic acid, undecylenic acid, lanolin fatty acid, isostearic acid, linolic acid, linolenic acid, and eicosapentaenoic acid.

Higher alcohols of straight/branched chain that can be mentioned include lauryl alcohol, cetyl alcohol, stearyl alcohol, behenyl alcohol, myristyl alcohol, oleyl alcohol, cetostearyl alcohol, monostearyl glycerine ether (batyl alcohol), 2-decyltetradecinol, lanolin alcohol, cholesterol, phytosterol, hexyldodecanol, isostearyl alcohol, octyldodecanol.

It may, for example, be that the diluent or carrier is oil or wax based and is selected from shea butter, cocoa butter, jojoba oil, olive oil, almond oil, macadamia nut oil, wheat germ oil, evening primrose oil and the like.

The composition may be an oil in water emulsion (o/w) or a water in oil emulsion (w/o).

In one embodiment, the diluent/carrier is present in an amount of from 0 to 99.9%, such as from 0.5 to 99.5%, or from 1 to 99% or from 2 to 98% or from 3 to 97% or from 5 to 95%. It may be that the diluent/carrier is present in an amount of from 5 to 90%, such as from 10 to 85% or from 12 to 80% or from 15 to 75% or from 20 to 70%.

In addition to the queen bee venom and any diluent/carrier, the composition may comprise other optional components. When present, compositions of the present invention may contain from about 0.0001% to about 50% by weight of the composition, of the optional components; e.g. from about 0.001% to about 40%, or from about 0.01% to about 30%, or from about 0.05% to about 20%, or from about 0.1% to about 15% or from about 0.5% to about 10%, by weight of the composition, of the optional components.

The Personal Care Product Council's International Cosmetic Ingredient Dictionary and Handbook, Thirteenth Edition, and the CTFA Cosmetic Ingredient Handbook, Second Edition (1992) each describe a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, plant extracts including essential oils, anti-caking agents, antifoaming agents, antimicrobials, binders, biological additives, buffering agents, bulking agents, chelating agents, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners/viscosity modifiers, vitamins, and combinations thereof.

In one embodiment the composition may further comprise other bee products in addition to the queen bee venom. Other bee products may, for example, comprise honey (e.g. manuka honey), propolis, honey wax, bee pollen, royal jelly, or combinations thereof. In one embodiment, one or more of honey, propolis and royal jelly is present in the composition.

In one embodiment, the composition comprises one or more plant extract. The plant extract may be selected from essential oils, extracts from leaves, extracts from stems, extracts from petals, extracts from seeds, extracts from roots and extracts from pollen.

In one embodiment, the composition comprises one or more essential oil.

The essential oil may be selected from basil oil, bay oil, bergamot oil, black pepper oil, cedarwood oil, chamomile oil, cinnamon oil, citronella oil, clary sage oil, eucalyptus oil, fenugreek oil, frankincense oil, geranium oil, ginger oil, grapefruit oil, jasmine oil, lavender oil, lemon oil, lemongrass oil, lime oil, mandarin oil, marjoram oil, melissa oil, myrrh oil, neem oil, neroli oil, orange oil, patchouli oil, peppermint oil, pine oil, rose oil, rosehip oil, rosemary oil, rosewood oil, sage oil, sandalwood oil, sassafras oil, spearmint oil, star anise oil, tangerine oil, tarragon oil, tea tree oil, thyme oil, ylang-ylang oil, and combinations thereof.

In one embodiment, the essential oil is selected from bergamot oil, cedarwood oil, chamomile oil, eucalyptus oil, fenugreek oil, frankincense oil, geranium oil, jasmine oil, lavender oil, lemon oil, marjoram oil, melissa oil, myrrh oil, neem oil, neroli oil, patchouli oil, rose oil, rosehip oil, rosemary oil, sage oil, sandalwood oil, tea tree oil, thyme oil, ylang-ylang oil, and combinations thereof.

In one embodiment, the essential oil is selected from eucalyptus oil, geranium oil, lavender oil, rose oil, rosemary oil, tea tree oil, and combinations thereof.

In one embodiment, the composition comprises one or more plant extract that is not an essential oil. It may be one or more extract obtained from plant leaves, stems, petals, seeds, roots and/or pollen. For example, it may be one or more extract obtained from plant leaves, stems, and/or roots.

In one embodiment, the plant extract is obtained from a plant selected from: aloe vera, basil, birch, burdock, comfrey, chamomile (including German chamomile), calendula, dandelion, echinacea, elderflower, green tea, fennel, horsetail, hyssop, lady's mantle, lavender, lemon balm, lime flower, linden, liquorice, marshmallow, nettle, Oregon grape, plantain, pomegranate, rose, rosemary, sage, St. John's wort, yarrow and witch hazel. The extract may be obtained from the plant's leaves, stems, petals, seeds, roots and/or pollen. For example, it may be obtained from the plant's leaves, stems, and/or roots.

In one embodiment, the plant extract is obtained from a plant selected from: aloe vera, comfrey, chamomile (including German chamomile), calendula, echinacea, fennel, green tea, horsetail, hyssop, liquorice, marshmallow, nettle, Oregon grape, pomegranate, and witch hazel. The extract may be obtained from the plant's leaves, stems, petals, seeds, roots and/or pollen. For example, it may be obtained from the plant's leaves, stems, and/or roots.

In one embodiment, the plant extract is obtained from a plant selected from: aloe vera, comfrey, chamomile (including German chamomile), calendula, echinacea, fennel, horsetail and marshmallow. The extract may be obtained from the plant's leaves, stems, petals, seeds, roots and/or pollen. For example, it may be obtained from the plant's leaves, stems, and/or roots.

In one embodiment, the plant extract is obtained from calendula. In particular it may be calendula absolute. The inclusion of calendula stimulates a stronger healing effect. In particular this may be useful for people with sensitive skins, as the desired effect can be achieved with a relatively low concentration of queen bee venom.

In one embodiment, the composition comprises one or more antioxidant.

The antioxidant may be selected from ascorbic acid and derivatives thereof, erythorbic acid and derivatives thereof, and tocopherols (vitamin E forms) and derivatives thereof.

Examples of ascorbic acid or derivatives thereof include ascorbic acid, sodium ascorbate, potassium ascorbate, calcium ascorbate, L-ascorbic acid phosphate ester, magnesium ascorbyl phosphate, sodium ascorbyl phosphate, ascorbyl sulfate, sodium ascorbyl 2 phosphate salt and ascorbyl-2-glucoside, and the like.

Examples of erythorbic acid or derivatives thereof include erythorbic acid or derivative thereof, such as erythorbic acid, sodium erythorbate, potassium erythorbate, calcium erythorbate, erythorbic acid phosphate, erythorbic acid sulfate and the like.

In general, suitable tocopherols include naturally occurring vitamin E, synthetic vitamin E, enantiomerically pure forms of vitamin E (e.g. (+)-alpha-tocopherol), vitamin E derivatives such as acetates, succinates, linoleate, more water-soluble forms of vitamin E such as tocophereth-5, tocophereth-10, tocophereth-12, tocophereth-18, tocophereth-50, D-alpha-tocopherol polyethylene glycol 1000-succinates. Specific examples of tocopherol or derivatives thereof include α-tocopherol, β-tocopherol, γ-tocopherol, δ-tocopherol, acetic acid-α-tocopherol, nicotinic acid-α-tocopherol, linoleic acid-α-tocopherol, succinic acid-α-tocopherol, as well as α-tocotrienol, β-tocotrienol, γ-tocotrienol, and δ-tocotrienol. Particular preference is given to naturally occurring vitamin E.

Other antioxidants that can be mentioned include flavonoids (catechin, anthocyanin, flavone, isoflavone, flavan, flavanone and rutin), phenolic acids (chlorogenic acid, ellagic acid, gallic acid and propyl gallate), lignans, curcumins and coumarins.

These compounds are contained in large amounts in extracts of certain natural substances, so they can be used in the form of extracts. Examples of extracts that can be used include licorice extract, cucumber extract, *Millettia dielsiana* extract, *Gentiana lutea* (Japanese gentian) extract, *geranium thunbergii* extract, cholesterol or derivative thereof, Chinese hawthorn extract, paeoniae radix extract, ginkgo extract, *Scutellaria baicalensis* extract, carrot extract, Turkestan rose (Ramanas rose) extract, *Cassia mimosoides* L. extract, tormentil extract, parsley extract, tree peony (peony root bark) extract, flowering quince (chaenomeles) extract, melissa extract, *Alnus firma* (cornflower) extract, strawberry begonia extract, rosemary extract, lettuce extract, tea extract (oolong tea, red tea, green tea, etc.), microbial fermentation metabolic products and *Siraitia grosvenorii* extract.

The composition may comprise a preservative. The composition may comprise a preservative selected from any of the group comprising phenoxyethanol; salicylic acid; potassium sorbate; DMDM hydantoin; benzyl alcohol; sodium benzoate; formaldehyde; chlorphenism; triclosan; imidazolidinyl urea; diazolidinyl urea; sorbic acid; methylisothiazolinone; sodium dehydroacetate; dehydroacetic acid; quaternium-15; stearalkonium chloride; zinc pyrithione; sodium metabisulfite; 2-bromo-2-nitropropane; chlorhexidine digluconate; polyaminopropyl biguanide; benzalkonium chloride; sodium sulfite; sodium salicylate; citric acid; grapefruit seed extract; neem oil; essential oil; lactic acid; and vitamin E (tocopherol); or combinations thereof.

The preservative may in one embodiment comprise methylchloroisothiazolinone.

In one embodiment, the composition does not comprise parabens.

The composition may optionally comprise one or more colouring. In one embodiment, the composition does not contain any added colours and takes its colour from the other ingredients present. In another embodiment, the composition includes natural colorants or pigments.

The composition may comprise one or more perfume. It may be that agents included for other properties, such as essential oils or rose water, also provide a perfuming effect.

In one embodiment, the perfume may be a natural perfume derived from animals, plants or minerals. Examples include rose extract, chamomile extract, green tea aromatic agent, lavender oil, geranium oil, jasmine oil, bergamot oil, musk oil, ylang ylang oil, limonene, linalol, citral, and rose oxide.

When the composition is oil-based, it may include oil-soluble components. Some oil-soluble components that can be mentioned include vitamin E agents, coenzyme Q agents and omega 3 oils (e.g. EPA, DHA, linoleic acid and other oils).

The composition constituents may be natural, non-synthetic, ingredients. It is understood that natural refers to ingredients that exist in or caused by nature and are not made or caused by humankind. Isolated, purified and/or concentrated forms of a natural ingredient may also be considered natural and non-synthetic.

According to another aspect of the present invention, there is provided a pharmaceutical composition for topical application to the skin, comprising the composition of the invention herein, and a pharmaceutically acceptable excipient or carrier.

According to another aspect of the present invention, there is provided a method of treatment or prevention of a skin condition, comprising the topical application of the composition according to the invention herein onto the skin of a subject afflicted with the skin condition, or at risk of being afflicted with the skin condition.

The skin condition may be selected from the group comprising skin ageing, elastosis, laxity (sagging), rhytids (wrinkles), skin infection, skin damage, skin burn, pain, and muscle tightness, and combinations thereof.

In one preferred embodiment, the composition is used in a method of cosmetically treating a skin condition selected from skin ageing, elastosis, laxity (sagging), and rhytids (wrinkles), and combinations thereof.

According to another aspect of the present invention, there is provided a composition according to the invention herein for use as a medicament.

According to another aspect of the present invention, there is provided a composition according to the invention herein for use in the treatment or prevention of a skin condition selected from: skin ageing, elastosis, laxity (sagging), rhytids (wrinkles), skin infection, skin damage, skin burn, pain, and muscle tightness.

In one preferred embodiment, the composition is used in relation to the treatment or prevention of a skin condition selected from skin ageing, elastosis, laxity (sagging), and rhytids (wrinkles), and combinations thereof.

According to another aspect of the present invention, there is provided a use of the composition according to the invention herein as a topical application on skin. The use may be cosmetic use.

According to another aspect of the present invention, there is provided a cosmetic treatment of the skin, comprising the application of the composition according to the invention herein on the skin.

The cosmetic treatment may be for alleviating or preventing the appearance of a skin condition selected from skin ageing, elastosis, laxity (sagging), rhytids (wrinkles), skin infection, skin damage, skin burn, pain, and muscle tightness.

In one preferred embodiment, the cosmetic treatment is used in relation to alleviating or preventing a skin condition selected from skin ageing, elastosis, laxity (sagging), and rhytids (wrinkles), and combinations thereof.

According to another aspect of the present invention, there is provided a face mask incorporating the composition according to the invention herein.

The face mask may comprise a cream, lotion or paste.

The face mask may be provided in the form of a composition that is to be applied directly to the skin to form a mask. The face mask may alternatively be provided in the form of a wrap impregnated or soaked in the composition, wherein the wrap is to be applied onto the skin.

The skilled person will understand that optional features of one embodiment or aspect of the invention may be applicable, where appropriate, to other embodiments or aspects of the invention.

SPECIFIC EXAMPLE OF THE INVENTION

Embodiments of the invention will now be described in more detail, by way of example only.

FIG. 1 shows a before and after photograph of the skin of a subject's arm after application of the composition of the invention.

EXAMPLE 1—ANTI-AGING

With reference to FIG. 1, approximately 5 ml of a formulation comprising 1 wt % queen bee venom (sourced from organic hives in Kenya) was applied to an area of a subject's skin, which has been showing the signs of ageing. The formulation was based on shea butter as a carrier and also included rose and lavender essential oils and manuka honey.

The formulation was applied twice daily for a week. After treatment, the skin looked visibly younger and wrinkles were reduced.

EXAMPLE 2—SKIN BURN

Approximately 5 ml of a formulation comprising queen bee venom was applied to an area of a dog's skin, which had been accidentally burnt due to excess sun exposure. The same formulation as in Example 1 was used.

The formulation was applied twice daily for 3 days. After treatment, the burned skin healed significantly.

The invention claimed is:

1. A cosmetic composition suitable for topical skin application to alleviate or prevent skin ageing, the composition comprising isolated queen bee venom and a diluent or carrier, wherein the composition is provided in the form of lotion, milk, mousse, serum, foam, gel, cream or ointment.

2. The composition according to claim 1, wherein the composition is a cream, or a gel.

3. The composition according to claim 1, wherein the composition comprises at least 0.11% queen bee venom.

4. The composition according to claim 3, wherein the composition comprises at least 0.5% queen bee venom.

5. The composition according to claim 4, wherein the composition comprises at least 1% queen bee venom.

6. The composition according to claim 5, wherein the composition comprises at least 10% queen bee venom.

7. The composition according to claim 6, wherein the composition comprises at least 50% queen bee venom.

8. The composition according to claim 1, wherein the composition comprises between about 1% and about 99% queen bee venom.

9. The composition according to claim 1, wherein the composition further comprises at least one of manuka honey, shea butter and essential oils, or combinations thereof.

10. The composition according to claim 1, wherein the composition further comprises one or more of abrasives, absorbents, fragrances, pigments, colorings/colorants, essential oils, anti-caking agents, antifoaming agents, antimicrobials, binders, biological additives, buffering agents, bulking agents, chelating agents, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners/viscosity modifiers, vitamins, or combinations thereof.

11. The composition according to claim 10, wherein the composition comprises the preservative methylchloroisothiazolinone.

12. The composition according to claim 1, wherein the composition does not comprise parabens.

13. The composition according to claim 1, wherein the composition constituents are natural, non-synthetic, ingredients.

14. A face mask incorporating the composition according to claim 1.

15. The composition according to claim 1, wherein the diluent or carrier comprises a material selected from the group consisting of de-ionized water, purified water, spring water, rose water and combinations thereof.

16. The composition according to claim 1, wherein the diluent or carrier comprises shea butter, cocoa butter, jojoba oil, olive oil, almond oil, macadamia nut oil, wheat germ oil, evening primrose oil, or combinations thereof.

17. The composition according to claim 1, wherein the composition further comprises one or more of honey, propolis and royal jelly.

18. The composition according to claim 1, wherein the composition further comprises one or more essential oils.

19. The composition according to claim 1, wherein the diluent or carrier comprises a material selected from the group consisting of oils, waxes, and combinations thereof.

20. A cosmetic composition suitable for topical skin application to alleviate or prevent skin ageing, the composition comprising: isolated queen bee venom; one or more of honey, propolis and royal jelly; one or more essential oils; and a diluent or carrier;
   wherein the diluent or carrier comprises shea butter, cocoa butter, jojoba oil, olive oil, almond oil, macadamia nut oil, wheat germ oil, evening primrose oil, or combinations thereof; and
   wherein the composition is provided in the form of a lotion, milk, mousse, serum, foam, gel, cream, or ointment.

21. A method of treatment or prevention of a skin condition, comprising the topical application of the composition according to claim 1 onto the skin of a subject afflicted with the skin condition, or at risk of being afflicted with the skin condition.

22. The method of claim 21, wherein the skin condition is skin ageing, elastosis, laxity (sagging), rhytids (wrinkles), skin infection, skin damage, skin burn, pain, and muscle tightness, or combinations thereof.

23. The method of claim 21, wherein the treatment or prevention of the skin condition comprises a cosmetic treatment of the skin to alleviate or prevent the appearance of the skin condition.

\* \* \* \* \*